United States Patent [19]

Scolastico et al.

[11] Patent Number: 5,281,586
[45] Date of Patent: Jan. 25, 1994

[54] L-α-GLYCEROPHOSPHORYL-D-MYO-INOSITOL FOR THE TREATMENT OF PERIPHERAL NEUROPATHIES AND OF CEREBROPATHIES

[75] Inventors: Carlo Scolastico; Camillo M. F. G. Palazzi; Carla Procida, all of Palazzo Tiepolo-Segrate, Italy

[73] Assignee: Apotekna S.A., Stabio, Switzerland

[21] Appl. No.: 836,337

[22] PCT Filed: Oct. 17, 1990

[86] PCT No.: PCT/EP90/01757
§ 371 Date: Mar. 2, 1992
§ 102(e) Date: Mar. 2, 1992

[87] PCT Pub. No.: WO91/06300
PCT Pub. Date: May 16, 1991

[30] Foreign Application Priority Data

Oct. 27, 1989 [IT] Italy ................... 22173-A/89

[51] Int. Cl.$^5$ ............................................ A61K 31/66
[52] U.S. Cl. ................................. 514/129; 558/177
[58] Field of Search ...................... 558/177; 514/129

[56] References Cited

FOREIGN PATENT DOCUMENTS 8400367  2/1984  World Int. Prop. O. .......... 558/177

OTHER PUBLICATIONS

Brown, D. M. et al. *J. Chem. Soc.* 1959, 3547–3552.
Clinton, E. et al. *Chem. Abstr.* 1963 58(4), 3644b.

*Primary Examiner*—Mary C. Lee
*Assistant Examiner*—Michael Ambrose
*Attorney, Agent, or Firm*—Mathews, Woodbridge & Collins

[57] ABSTRACT

Pharmaceutical compositions for the treatment of peripheral neuropathies of dysmetabolic or toxic origin and of cerebropathies of organic and functional origin, containing as the active ingredient L-α-glycerophosphoryl-D-myo-inositol, as such or as the alkali or alkali-earth metal salt thereof.

2 Claims, No Drawings

L-α-GLYCEROPHOSPHORYL-D-MYO-INOSITOL FOR THE TREATMENT OF PERIPHERAL NEUROPATHIES AND OF CEREBROPATHIES

The present invention relates to pharmaceutical compositions for the treatment of peripheral neuropathies of dysmetabolic or toxic origin, and of cerebropathies of organic and functional origin, containing as the active ingredient L-α-glycerophosphoryl-D-myo-inositol (hereinafter called GFI) of formula 1 or the alkali or alkaline-earth metal salts thereof.

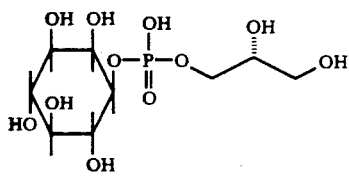

The present invention also relates to the alkali and alkaline-earth metal salts of GFI, particularly the calcium salt of GFI.

From a chemical point of view, GFI is structurally similar to phosphatidylinositol (hereinafter called FI); FI being the double-acylated product with fatty acids, mainly unsaturated acids, at the hydroxy groups of the glycerine residue of glycerophosphorylinositol.

FI is a molecule of natural origin, almost unsoluble in water, which is generally extracted from bovine brain and/or soy-bean, in admixture with phosphatidylethanolamine ("cephalinic fraction") and subsequently purified.

FI turns out to be rather unstable, since the unsaturated fatty acid chains bound to the hydroxy groups of the glycerin residue easily undergo peroxydation reactions, yielding a number of decomposition products.

On the contrary, GFI is the deacylated analogue and therefore it is water-soluble as such or salified, it is stable and the alkali and alkaline-earth metal salts thereof, specifically the sodium, potassium, calcium and magnesium salts, are crystalline and particularly suited for use in pharmaceutical formulations.

The advantages involved in the use of said salts, particularly the calcium salt, compared with the free acid GFI, consist in a lower hygroscopicity, a higher stability, a better adaptability to the use thereof in pharmaceutical compositions, since the salts themselves, being poorly hygroscopic, can be preserved for a long time without appreciable decompositions.

GFI, or the salts thereof with alkali and/or alkaline-earth metals, particularly the calcium salt, are obtained by controlled saponification of the acylated phospholipid mixture contained in soy-bean, subsequent separation with purification of the obtained free acid GFI and optionally salification with alkali and/or alkaline-earth metals.

A known method for the preparation of GFI is described in EP-A-0.217.765.

From a biochemical point of view, FI catabolism is known to play a very important role in the biochemical events connected with physiological activity, as far as phosphorus turnover is concerned (Ansell G. B. and Dohmen H.; J. Neurochem. 2, 1, 1957; Sheltaway A. and Dawson R. M. C.; Biochem. J., 111, 157, 1969).

When calcium is available as a support for the activity of phosphatidylinositol phosphodiesterase (phospholipase C), this enzyme is probably the main responsible for FI degradation (Friedel R. O., Brown J. D. and Durrell J.; Biochim. biophys. Acta., 144, 684, 1967; Keough K. M. W. and Thompson W.; Biochim. biophys. Acta., 270, 324, 1972; Thompson W.; Can. J. Biochem., 45, 853, 1967; Dawson R. M. C. et al.; Biochem. J., 122, 605, 1971; Irvine R. F.; Biochem. J., 176, 475, 1978), the main metabolits of which are diacylglycerole and inositolphosphate; the whole metabolic cycle (Hawthorne J. N. and Pickard M. R.; J. Neurochem., 32, 5, 1979) can be represented as follows:

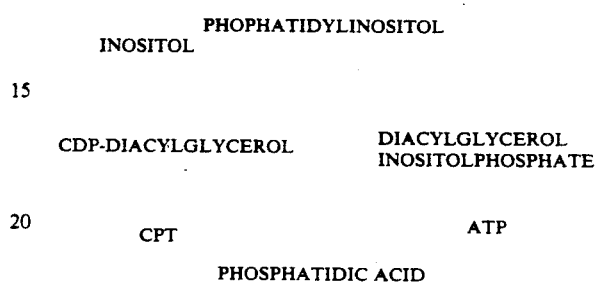

Even though a poor acylation of FI can occur under particular physiological conditions (low $Ca^{++}$ concentration), which acylation being catalysed by the enzyme phospholipase $A_1$ and giving raise to lysophosphatidylinositol (Hong S. L. and Deykin D.; J. Biol. Chem., 256, 5215, 1981), the specificity of phosphatidylinositol phosphodiesterase, the ubiquitous distribution in animal cells and the extremely high activity thereof, evidenced also in vitro (Friedel R. O. Brown J. D. and Durrell J.; Biochim. biophys. Acta., 144, 684, 1967; Keough K. M. W. and Thompson W.; Biochim. biophys. Acta., 270, 324, 1972; Thompson W.; Can. J. Biochem., 45, 853, 1967; Dawson R. M. C. et al.; Biochem. J., 122, 605, 1971; Irvine R. F.; Biochem. J., 176, 475, 1978), make this enzyme the main responsible for phosphoinositidic metabolism.

Now, it has been found that GFI has a marked activity in peripheral neuropathies of dysmetabolic or toxic origin and in cerebropathies of organic and functional origin.

The results from pharmacological experimentation are reported hereinbelow, by way of examples.

EXAMPLE 1

Activity of GFI in the Enteric Autonomic Neuropathy of Diabetic Origin

The neurological correlates of diabetes have been clearly described as functional and morphological alterations of both sensory and motor peripheral nerves.

These abnormalities are underlined by significant changes of axonal transport with a concomitant axonal atrophy that is followed by degeneration.

The autonomic diabetic neuropathy is associated with gastrointestinal problems such as diabetic diarrhea, constipation, reduced small intestinal transit and megacolon, and with an altered innervation of the gut.

Alloxan-induced experimental diabetes shows a remarkable correlation between neuronal and gastrointestinal alterations.

Substance P, met-enkephalin and VIP are contained in enteric neurons with different projections and different activities. Substance P and VIP axons project orally, while enkephalin neurons project anally. Substance P produces direct excytation of enteric neurons and smooth muscle, while enkephalin produces inhibition of enteric neurons and muscle contraction by a direct action, although an indirect effect through acetylcholine stimulation cannot be excluded. VIP has smooth muscle relaxant activity. The gastrointestinal functions are likely regulated by the fine interplay among these neuronal components. In the diabetic autonomic neuropathy of the gut such coordinated activity is altered thus compromising the gastrointestinal functions.

The test was carried out on male Sprague Dowley rats (weighing about 250 g) divided in 3 groups: a control group (C), a diabetic group (D) and a treated diabetic group (DDTRp). Diabetes was induced by single subcutaneous injection of 100 mg/kg alloxan (glycemia >400 mg/dl) and, starting from the seventh day after diabetic induction, treatment was carried out subcutaneously with 10 mg/kg of $(GFI)_2Ca$ for three months.

The following parameters were measured: body weight, blood glucose, met-enkephalin, substance P and VIP.

All of these parameters, being substantially affected in the diabetic group, were restored in the treated diabetic group and turned out to be similar to those of the respective control group, with statistically significant variations.

Tables 1 and 2 show the met-enkephalin and substance P values measured during the test.

Besides all rats of the diabetic group D show a typical cataract: the crystalline was very fragile and crumbled during dissection. In the contrary crystalline of diabetic group DDTRp was clear and normally resistant to dissection procedure.

TABLE 1

MET-ENKEPHALIN (pg/mg prot.)

SMALL INTESTINE

| | pg/mg prot. |
|---|---|
| Duodenum | |
| C | 141.5 ± 16.7 (n = 6) |
| D | 58.6 ± 3.9 (n = 7)*** |
| DDTRp | 103.9 ± 14.7 (n = 8)n.s. |
| Jejunum | |
| C | 45.9 ± 4.8 (n = 6) |
| D | 15.1 ± 1.9 (n = 8)*** |
| DDTRp | 34.9 ± 1.8 (n = 8)* |
| Ileum | |
| C | 27.9 ± 1.5 (n = 6) |
| D | 10.6 ± 1.3 (n = 6)*** |
| DDTRp | 24.9 ± 1.7 (n = 7)n.s. |

C = Control group
D = Diabetic group
*p < 0.05
***p < 0.001
DDTRp = D post-treated with $(GFI)_2Ca$ n.s. = not significant

LARGE INTESTINE

| | pg/mg prot. |
|---|---|
| Rectum | |
| C | 102.4 ± 11.8 (n = 5) |
| D | 78.7 ± 5.1 (n = 7)** |
| DDTRp | 120.0 ± 1.6 (n = 8)n.s. |
| Colon | |
| C | 101.0 ± 10.2 (n = 7) |
| D | 46.2 ± 3.8 (n = 8)*** |
| DDTRp | 90.5 ± 5.6 (n = 8)n.s. |

C = Control group
D = Diabetic group
*p < 0.01
***p < 0.001
DDTRp = D post-treated with $(GFI)_2Ca$ n.s. = not significant

TABLE 2

SUBSTANCE P (ng/mg prot.)

SMALL INTESTINE

| | ng/mg prot. |
|---|---|
| Duodenum | |
| C | 1.17 ± 0.091 (n = 8) |
| D | 0.44 ± 0.025 (n = 7)*** |
| DDTRp | 1.00 ± 0.081 (n = 8)n.s. |
| Jejunum | |
| C | 1.43 ± 0.1 |
| D | 0.78 ± 0.05*** |
| DDTRp | 1.31 ± 0.04 n.s. |
| Ileum | |
| C | 1.22 ± 0.06 |
| D | 0.39 ± 0.03 *** |
| DDTRp | 1.13 ± 0.09 n.s. |

C = Control group
D = Diabetic group
*p < 0.001
n.s. = non significant
DDTRp = D post-treated with $(GFI)_2Ca$

LARGE INTESTINE

| | ng/mg prot. |
|---|---|
| Caecum | |
| C | 0.76 ± 0.05 |
| D | 0.37 ± 0.02*** |
| DDTRp | 0.50 ± 0.02** |
| Colon | |
| C | 0.58 ± 0.02 |
| D | 0.35 ± 0.02*** |
| DDTRp | 0.56 ± 0.03 n.s. |
| Rectum | |
| C | 0.54 ± 0.03 |
| D | 0.34 ± 0.02*** |
| DDTRp | 0.55 ± 0.02 n.s. |

C = Control group
D = Diabetic group
*p < 0.01
***p < 0.001
DDTRp = D post-treated with $(GFI)_2Ca$ n.s. = not significant

EXAMPLE 2

Activity of GFI in Early Enteric Autonomic Neuropathy of Diabetic Origin

Experimentally induced diabetic rats will be treated according to the above said modalities (see EXAMPLE 1) to evaluate the gastroenteric protection in the same moment in which the neuropathic damage is established.

Treatment was carried out i.p. with 10 mg/Kg of $(GFI)_2Ca$ for 35 days, starting from the seventh day after diabetic induction. The observed parameters (body weight, blood glucose and met-enkephalin) were reestablished in the treated diabetic group DDTRp in a similar way as described in EXAMPLE 1.

EXAMPLE 3

Activity on Receptor and Second Messenger in Peripheral Organs in Experimental Diabetic Neuropathy The animals, treatment, groups and dosage are similar to those reported in EXAMPLE 1, while days of treatment are 35 like in EXAMPLE 2.

The measured parameter was insulin receptor in liver, by binding of $^{125}I$-insulin, analized by the method of Scatchard (G. Scatchard; Ann. N.Y. Acad. Sci.; 51, 660, 1970), using purified hepatic plasma membranes, prepared by the method of Ray (T. K. Ray; Biochem. Biophys. Acta; 196, 1, 1970).

The number of high affinity receptor binding sites for $^{125}I$-insulin ($B_{maxI}$) in liver is increased in diabetic rats.

The treatment with (GFI)₂Ca prevents partially this increase in diabetic rats.

EXAMPLE 4

Anti-amnesic Activity of GFI Using a One-Trial Passive Avoidance Test with Electro-Convulsive Shock as the Amnesic Agent.

This passive avoidance test was carried out using a conventional apparatus consisting of a chamber with a grid floor and an elevated runway protruded from the front wall of the chamber. The runway is illuminated while the chamber is dark. When placed on the runway a rat can enter the dark chamber through an opening. A scramble footshock can be delivered through the grid floor of the dark compartment. The test was subdivided during 3 days: on the first day, each rat was subjected to the usual learning training; on the second day, the treated group was administered orally with (GFI)₂Ca at three dose levels: 3-30-100 mg/kg, and after 60 min., training was carried out by means of both the footshock, as a further learning agent, and electro-shock, as the amnesic agent. On the third day, training was repeated measuring the latency time necessary for the rat to enter the room.

The test was carried out in comparison with Piracetam, administered at doses of 300-1000 mg/kg per os, and significance of the results in favour of GFI was evidenced comparing the doses of 30-100 mg/kg of GFI with those of 300-1000 mg/kg of Piracetam.

EXAMPLE 5

Activity of GFI in the Nerve Conduction Velocity

Male Fischer F-344 rats with an initial weight of 271 g were used. The diabetes was induced with 70 mg/Kg of streptozocin and, in order to prevent an uncontrolled deterioration of the general physiological state of the diabetic animals, they were given daily s.c. injections of 0.75 U insulin. The animals were assigned to the three groups C, D and DDTRp (see EXAMPLES 1, 2, 3).

The treatment was performed with (GFI)₂Ca 10 mg/Kg i.p. for 8 weeks, starting from the first day of diabetes. The measured parameter was the tail nerve conduction velocity (CV) as reported by Spüler et al. (M. Spüler, W. Dimpfel, H. -U. Tüllner; Arch. Int. Pharmacodyn., 287, 211, 1987). In particular it was evaluated:

1. The CV of proximal section of motor nerve
2. The CV of proximal section of sensory nerve
3. The CV of distal section of sensory nerve The CV was measured before induction of diabetes (3 month old rats) and after 8 weeks of treatment. It decreased in diabetic group D which confirmed the development of a peripheral diabetic neuropathy, while, as reported in table 3, in DDTRp group it was statistically increased, suggesting the therapeutic effect of (GFI)2Ca in diabetic neuropathy.

of test was positively performed in the past treating streptozotocin-induced diabetic rats with 650 mg/Kg of myo-inositol, but this result was not confirmed later by other tests, although the doses of myoinositol were always very high (J. G. Salway, J. A. Finnegan, D. Barnett, L. Whitehead, A. Karunanayaka and R. B. Payne; 2, 1282, 1978. For this reason the possible therapeutic use of myo-inositol failed.

As it is evident from the above results, GFI can conveniently be used as the active ingredient in pharmaceutical compositions for the treatment of peripheral neuropathies and of cerebropathies of organic or functional origin, such as vasculopathies, Alzheimer disease, involutive syndromes in the elderly and similar pathologies.

Examples of pharmaceutical compositions suited to the oral administration comprise capsules, soft capsules, tablets, granulates, powders, solutions, sachets, sustained-release forms, containing 10 to 500 mg of GFI (as such or as an alkali or alkaline-earth metal salt, preferably as the calcium salt), per unitary dose, to be administered 2-3 times a day, according to the diagnosis and the patient's conditions.

For the parenteral administration, both intravenous and intramuscular, suited forms are lyophilized vials or sterile solutions containing 2 to 250 mg of GFI (as such or as an alkali or alkaline-earth metal salt, preferably as the calcium salt), per unitary dose, to be administered 1 to 3 times a day.

The compositions of the invention can possibly contain other active ingredients having a complementary or anyhow useful activity.

The physico-chemical characteristics of GFI and of the calcium salt thereof used in the above described pharmacological tests and prepared according to the above reported conventional procedures are shown hereinbelow, by way of examples.

GFI free acid MW = 334 g/mole.
m.p. = 140° C.

Elemental Analysis:

C (theoretical: 32.33%) = 32.25%.
H (theoretical: 5.69%) = 5.73%.
GFI calcium salt (GFI)₂Ca; MW = 706 g/mole.
[α]$_D$ = −15.5° ±1 (c=2.07; H₂O).
¹H-NMR (300 MHz; D₂O):

TABLE 3

|   | CV ± SEM (m/s) of proximal section of motor nerve | | CV ± SEM (m/s) of proximal section of sensory nerve | | CV ± SEM (m/s) of distal section of sensory nerve | |
|---|---|---|---|---|---|---|
|   | baseline | 8 weeks | baseline | 8 weeks | baseline | 8 weeks |
| C | 32.2 ± 0.2 | 33.2 ± 0.7 | 41.2 ± 0.2 | 43.1 ± 0.6 | 35.7 ± 0.4 | 36.2 ± 0.8 |
| D | 32.1 ± 0.4 | 28.1 ± 0.8* | 40.8 ± 0.3 | 35.9 ± 0.7* | 35.2 ± 0.6 | 30.5 ± 0.4* |
| DDTRp | 31.8 ± 0.5 | 32.1 ± 0.4* | 40.6 ± 0.8 | 42.6 ± 0.8* | 35.1 ± 0.7 | 35.9 ± 0.9* |

*p < 0.001 D vs. C and DDTRp vs. D

It is known (D. A. Green, P. V. de Jesus and A. I. Winegrad; J. Clin. Invest., 55, 1326, 1975) that this kind ppm 3.37 (dd; CH-5; $J_{5-6}=J_{5-4}=9.27$ Hz)
ppm 3.58 (dd; CH-3; $J_{3-2}=2.78$ Hz; $J_{3-4}=9.27$ Hz)
ppm 3.65–3.75 (m; CH-4+CH$_2$-9)
ppm 3.79 (dd; CH-6; $J_{6-5}=J_{6-1}=9.27$ Hz)
ppm 3.90–4.10 (m; CH-1+CH-8+CH$_2$-7)
ppm 4.31 (dd; CH-2; $J_{2-3}=J_{2-1}=2.78$ Hz)
ppm 4.80 (s; DHO)
$^{13}$C-NMR (D$_2$O) (fully decoupled)
ppm 69.03 (s; C-9)
ppm 73.34 (d; C-7; $J_{C-O-P}=5.6$ Hz)
ppm 77.60 (d; C-8)
ppm 77.71 (s; C-3)
ppm 78.25 (m; C-2+C-6)
ppm 79.16 (s; C-4)
ppm 80.88 (s; C-5)
ppm 83.13 (d; C-1; $J_{C-O-P}=5.9$ Hz)

Elemental Analysis:

C (theoretical: 30.59%)=30.48%.
H (theoretical: 5.10%)=5.15%.

We claim:

1. A method for treating peripheral neuropathies of dysmetabolic or toxic origin and cerebropathies of organic and functional origin which comprises administering to a patient an effective amount of L-α-glycerophosphoryl-D-myo-inositol or an alkali or alkaline-earth metal salt thereof.

2. A method for treating peripheral neuropathies of dysmetabolic or toxic origin and cerebropathies of organic and functional origin which comprises administering to a patient an effective amount of L-α-glycerophosphoryl-D-myo-inositol calcium salt.

* * * * *